(12) United States Patent
Jowett et al.

(10) Patent No.: US 9,179,895 B2
(45) Date of Patent: Nov. 10, 2015

(54) ORAL FLUID COLLECTION DEVICE

(75) Inventors: Gordon Jowett, Witney (GB); Andrew Woodhead, Monmouth (GB)

(73) Assignee: Concateno UK Limited (GB)

( * ) Notice: Subject to any disclaimer, the term of this patent is extended or adjusted under 35 U.S.C. 154(b) by 625 days.

(21) Appl. No.: 13/256,884

(22) PCT Filed: Mar. 16, 2010

(86) PCT No.: PCT/EP2010/053378
§ 371 (c)(1),
(2), (4) Date: Dec. 8, 2011

(87) PCT Pub. No.: WO2010/106061
PCT Pub. Date: Sep. 23, 2010

(65) Prior Publication Data
US 2012/0071789 A1    Mar. 22, 2012

(30) Foreign Application Priority Data
Mar. 18, 2009  (GB) .................................. 0904631.9

(51) Int. Cl.
*A61B 10/00*    (2006.01)

(52) U.S. Cl.
CPC ....... *A61B 10/0051* (2013.01); *Y10T 29/49826* (2015.01)

(58) Field of Classification Search
CPC .................................................. A61B 10/0051
USPC .......................................................... 600/573
See application file for complete search history.

(56) References Cited

U.S. PATENT DOCUMENTS

| 6,365,417 B1 * | 4/2002 | Fleming et al. ............... 436/514 |
| 6,423,550 B1 * | 7/2002 | Jenkins et al. ................ 436/518 |
| 2003/0064526 A1 | 4/2003 | Niedbala et al. |
| 2006/0013738 A1 | 1/2006 | Ramsey |
| 2006/0292034 A1 | 12/2006 | Gould et al. |

FOREIGN PATENT DOCUMENTS

| EP | 0 734 684 A1 | 10/1996 |
| EP | 1 553 394 A1 | 7/2005 |
| GB | 2440353 B | 3/2011 |
| WO | 2008/131033 A1 | 10/2008 |
| WO | 2008/139324 A2 | 11/2008 |

OTHER PUBLICATIONS http://www.merriam-webster.com/dictionary/tend, Definition of tend, downloaded Jul. 10, 2014, 3 pages.*
International Search Report prepared for International Application No. PCT/EP2010/053378 by the European Patent Office as International Searching Authority, mailed May 21, 2010, 6 pages.
Search Report under Section 17 of the Patents Act 1997, prepared by the United Kingdom Intellectual Property Office for Great Britain Patent Application No. GB0904631.9, Jul. 6, 2009, 1 page.

* cited by examiner

*Primary Examiner* — Lee S Cohen
*Assistant Examiner* — Emily Lloyd
(74) *Attorney, Agent, or Firm* — Swanson & Bratschun, L.L.C.

(57) ABSTRACT

According to a first aspect of the present invention there is provided an oral fluid collection device. The oral fluid collection device comprises a handle, a swab holder, and a swab. The swab is in the form of a hollow tube of absorbent material coaxially located about the swab holder, such that the swab is supported by the swab holder along the entire length of the swab.

18 Claims, 6 Drawing Sheets

ORAL FLUID COLLECTION DEVICE

CROSS-REFERENCE TO RELATED APPLICATIONS

This application is a 35 USC 371 of PCT Application Serial No. PCT/EP2010/053378, filed Mar. 16, 2010, currently pending, entitled "Oral Fluid Collection Device," which claims priority to Great Britain Patent Application No. 0904631.9, filed Mar. 18, 2009, entitled "Oral Fluid Collection Device," each of which is incorporated herein in its entirety by reference.

FIELD OF THE INVENTION

The present invention relates to an oral fluid collection device.

BACKGROUND

Oral fluid is now often used as a diagnostic matrix for the detection of analytes such as antibodies, antigens, hormones and pharmaceutical drugs including drugs of abuse. The main advantages of oral fluid over other biological fluids are that oral fluid is easily accessible by non-invasive means, does not require experience in collection, as is the case with blood, and can be easily collected under observation. As such, oral fluid is used in laboratory-based and point-of-care tests for the detection of drugs of abuse, viruses and bacteria like HIV and Helicobacter pylori, therapeutic drug monitoring and DNA typing. Oral fluid is now also the preferred and most convenient matrix for testing motorists driving under the influence of drugs.

It is desirable that the procedure for using oral fluid as a diagnostic matrix should involve a rapid collection phase (important for on-site testing), the collection of a sufficient volume for immediate and subsequent analysis, and the ability to extract the analyte under investigation from the oral fluid.

Usually, oral fluid is collected by placing some form of an absorbent material in the mouth followed by extraction of the oral fluid from the absorbent material, which can be made of cotton, cellulose, rayon or any other suitable material. There are several devices described in the prior art for the collection of oral fluid. For example, WO2006/064285 describes an analyte collection apparatus that can be used for collecting oral fluid, wherein an absorbent pad is releasably gripped by a set of fingers at the end of a handle. As such, this device requires that the absorbent material is robust enough to swab a subject's mouth without the risk of mechanical failure of the material during the process, and therefore that the absorbent material is of a sufficiently high density to provide this robustness. However, the higher the density of the absorbent material, the slower rate of the sample collection and the poorer the analyte recovery. The higher density of the absorbent material therefore compromises the performance of its saliva collection function. Furthermore, the device has no means of indicating that a sufficient volume of saliva has been collected.

WO2008/012566 describes a device for the collection of oral fluid wherein a cotton or rayon swab is woven onto the end of a shaft. A glaze may then be applied over the surface of the swab to prevent disintegration of the swab in use. Without the glaze the swab would be required to be of sufficiently high density to prevent disintegration. In either case, the high density of the material or the applied glaze causes a reduction in the saliva collection performance of the device.

SUMMARY

According to a first aspect of the present invention there is provided an oral fluid collection device. The oral fluid collection device comprises a handle, a swab holder, a swab and a wick. The swab is in the form of a hollow tube of absorbent material coaxially located about the swab holder, such that the swab is supported by the swab holder along the entire length of the swab. The wick is located within the swab holder and is in fluid communication with the swab, the wick containing a soluble dye for the purpose of providing a fluid adequacy indication during use. The swab may be a spun polyester capillary structure.

The swab holder may further comprise an at least partially hollow core accommodating said wick, an opening passing through a wall of the swab holder into the hollow core, and a projection on an inner surface of the hollow core opposite the opening and which tends to press the wick through the opening and into contact with the swab. The projection may be a ramp inclined so as to guide the wick through the opening during insertion of the wick into the swab holder.

Alternatively, the swab holder may further comprise an at least partially hollow core, and a capillary passing through a wall of the swab holder into the hollow core which tends to carry fluid between the swab and the wick.

The swab holder and said handle may be formed as two separate parts, which are connected together in use. The handle may be substantially transparent at least in the region of an end of the wick and the swab holder may be opaque. The swab holder may obscure a portion of the wick coated or impregnated with said soluble dye.

The swab holder may be provided with one of a plug or a socket and the handle provided with the other of a plug or a socket, the swab holder and the handle being connected by means of a mechanical fit formed between the plug and the socket.

According to a second aspect of the present invention there is provided a method of manufacturing an oral fluid collection device. The method comprises locating a swab in the form of a hollow tube of absorbent material about a swab holder, such that the swab is supported by the swab holder along the entire length of the swab, either before or after locating the swab, inserting a wick into a passage within the swab holder such that at one end the wick extends out of an open end of said passage and at the other end the wick is in fluid communication with said swab, the wick being at least partially coated or impregnated with a dye, and connecting the swab holder to a handle.

During insertion of the wick, a projection on an inner surface of the passage within the swab holder may guide the wick through an opening in the swab holder and into contact with the swab.

The swab may be attached to the swab holder using a mechanical fit or a plastic welding process such as laser or ultrasonic or microwave welding. The swab holder may be connected to the handle using a mechanical fit or a plastic welding process such as laser or ultrasonic or microwave welding.

If the swab holder is connected to the handle using a mechanical fit, the mechanical fit may be achieved by the insertion of a plug formed with one of the swab holder or the handle being inserted into a socket formed with the other of the swab holder or the handle.

According to a third aspect of the present invention there is provided a testing kit comprising an oral fluid collection device and a container arranged to receive the oral fluid collection device. The container may contain a buffer solution.

The testing kit may also comprise means for holding the oral fluid collection device inside the container, following insertion of the oral fluid collection device into the container. By way of example, the means for holding the oral fluid collection device inside the container may be provided by a snap fit or an interference fit between the container and the oral fluid device.

DETAILED DESCRIPTION

Figure 1:
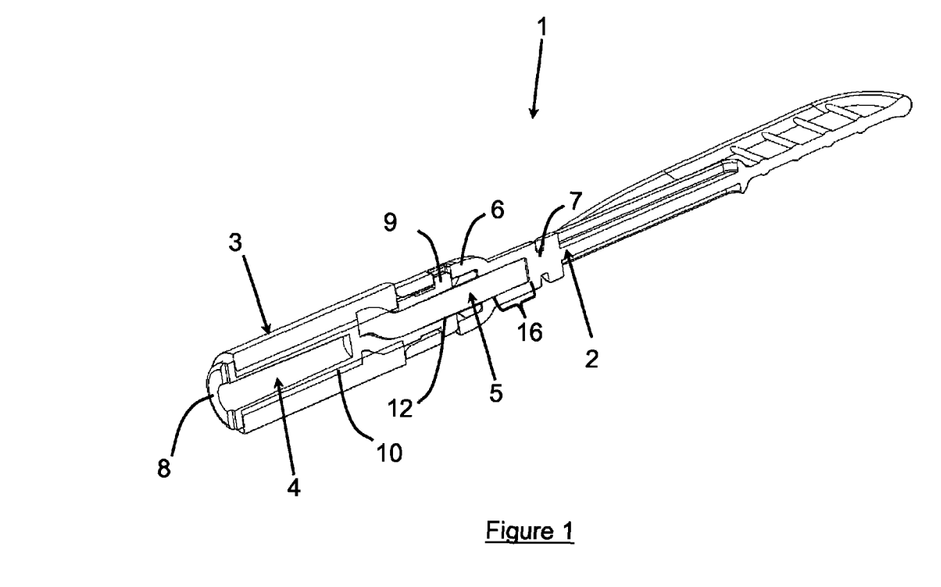
FIG. 1 is a cross-sectional view through an oral fluid collection device.
Figures 2, 3:
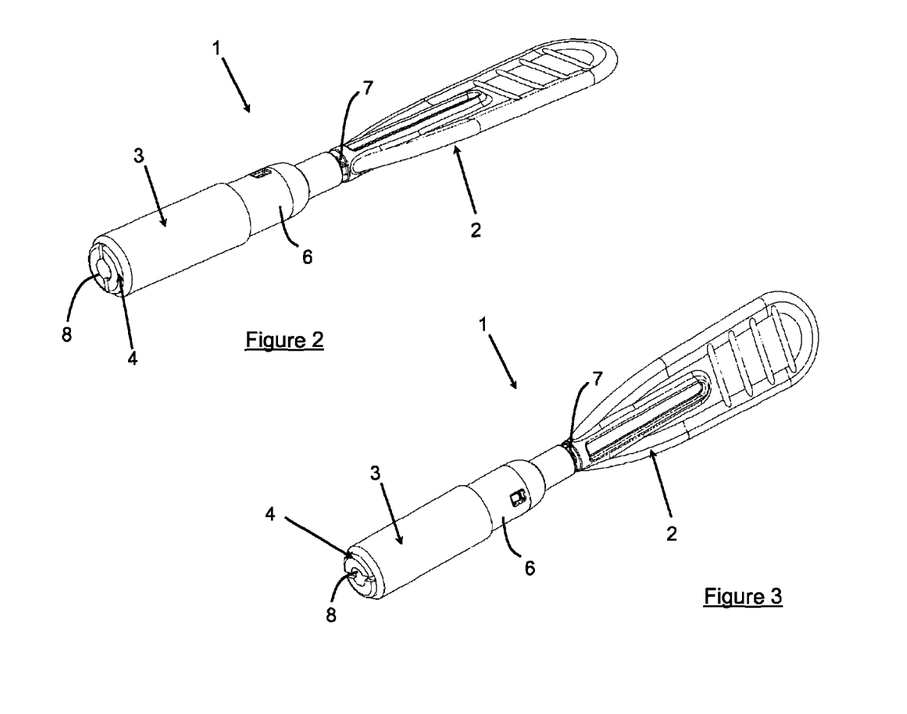
FIG. 2 is a perspective view of the oral fluid collection device of FIG. 1.
FIG. 3 is a perspective view of the oral fluid collection device of FIG. 1 rotated through 90 degrees.

There is illustrated in FIGS. 1, 2 and 3 an oral fluid collection device 1, the oral fluid collection device 1 comprising four separately formed components, namely a handle 2, a collection swab 3, a swab holder 4 and an indicator wick 5.

The handle 2 comprises a rigid, elongate, transparent, injection-moulded plastic component. By way of example, the handle 2 could be made of acrylonitrile butadiene styrene (ABS) or polystyrene. One end of the handle 2 is formed into a socket 6. The handle 2 is also formed with a 'break-off' point 7 connecting the socket 6 to the body of the handle 2 such that it can be separated from the rest of the device 1.

Figure 4:
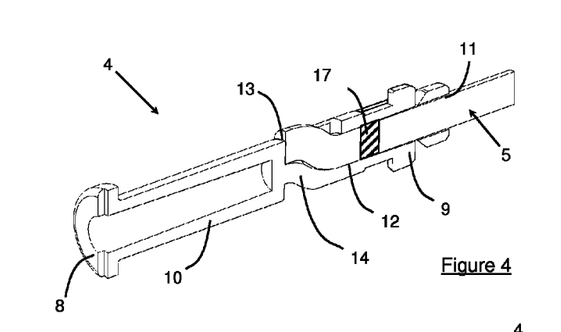
FIG. 4 is a cross-sectional view through the collection swab core and the indicator wick of the oral fluid collection device of FIG. 1.
Figure 5:
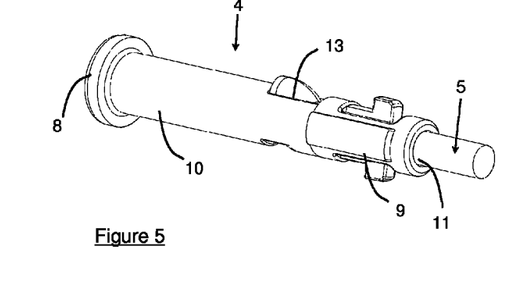
FIG. 5 a perspective view of the collection swab core and the indicator wick of the oral fluid collection device of FIG. 1.
Figure 6:
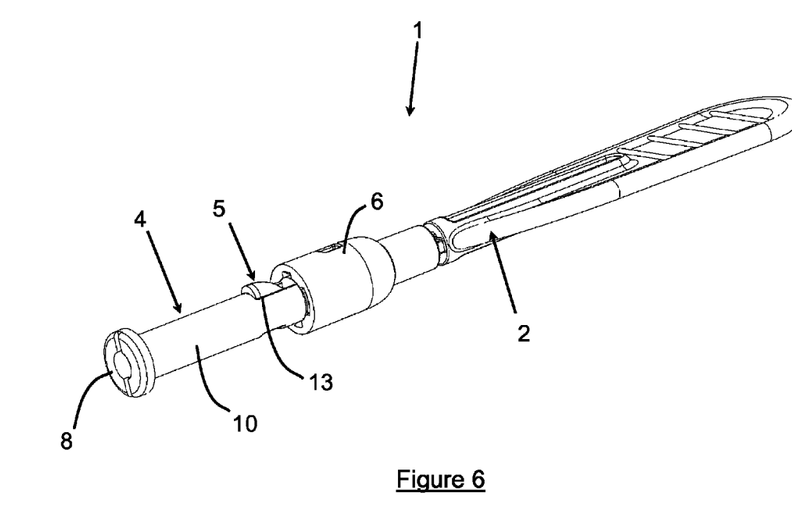
FIG. 6 is a perspective view of the oral fluid collection device of FIG. 1 without a collection swab.

FIGS. 4 and 5 illustrate the swab holder 4. The swab holder 4 is a rigid, elongate, opaque, injection-moulded plastic component. By way of example, the swab holder 4 could be made of acrylonitrile butadiene styrene (ABS) or polystyrene. One end of the swab holder 4 is formed into a flat stop 8. The opposing end of the swab holder 4 is formed into a plug 9 for insertion into the socket 6 of the handle 2. Between the flat stop 8 and the plug 9, the swab holder 4 is formed into a cylindrical rod 10. The cylindrical rod 10 forms the core of the collection swab 3. The plug 9 is also formed with an open end 11 that opens into a hollow wick channel 12 within the swab holder 4. The wick channel 12 extends from the open end 11 of the plug 9 to a wick opening 13 formed in the side of the cylindrical rod 10. The swab holder 4 is also formed with an inclined ramp 14 extending from the interior of the wick channel 13 up towards the exterior surface of the cylindrical rod 10.

The collection swab 3 is a spun polyester capillary structure that is formed as a hollow tube or cylinder. The indicator wick 5 can also be a spun polyester capillary structure that can be manufactured using the same process as the collection swab 3. However, the indicator wick 5 can be of a different density to the swab 3. At a point along its length, the indicator wick 5 is impregnated with a band of dye 17.

The device 1 is assembled by insertion of the indicator wick 5 into the wick channel 12 of the swab holder 4. As the wick 5 is inserted it makes contact with the ramp 14. Further insertion of the wick 5 causes it to ride up the ramp 14 and project through the wick opening 13. When the end of the wick 5 makes contact with the end of the wick channel 12, the wick 5 is fully inserted. The wick 5 is of sufficient length that, when fully inserted into the wick channel 12, one end of the wick 5 projects out from the open end 11 of the plug 9 (see FIGS. 4 and 5).

The hollow cylindrical collection swab 3 is then pushed onto the cylindrical rod 10 of the swab holder 4 over the plug 9. The stop 8 prevents the swab 3 from moving beyond the end of the swab holder 4. Alternatively, the swab 3 could be held in place on the cylindrical rod 10 using some other mechanical fit, or the swab 3 could be attached to the cylindrical rod 10 using a plastic welding process such as laser, ultrasonic or microwave welding. The plug 9 can then be inserted into socket 6 of the handle 2. The plug 9 and socket 6 form a mechanical snap-fit to connect the swab holder 4 to the handle 2. Alternatively, the two components could be connected using a plastic welding process such as laser, ultrasonic or microwave welding.

Figure 10:
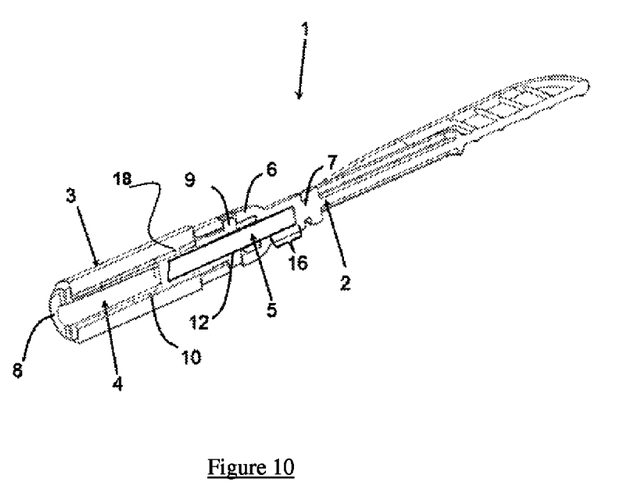
FIG. 10 is a cross-sectional view through an oral fluid collection device.

Once the handle 2 and the swab holder 4 have been assembled and connected together, the indicator wick 5 runs from the wick opening 13, along the wick channel 12, and projects out from open end 11 of the plug 9 into the hollow socket 6. In doing so, the opaque swab holder 4 shrouds that portion of the wick 5 that is within the wick channel 12, such that the only visible portion 16 of the wick 5 is that portion which projects out from open end 11 of the plug 9 and can be seen through the transparent handle 2 (see FIG. 1). As the inclined ramp 14 acts to push the end of the indicator wick 5 out through the wick opening 13 and against the collection swab 3, the swab 3 and the wick 5 are in fluid communication. As an alternative to the wick opening 13 and the inclined ramp 14, fluid communication between the swab 3 and the wick 5 could be achieved by providing a capillary 18 formed in the side of the cylindrical rod 10, see FIG. 10.

In use, a user holds the handle 2 of the device 1 and inserts the collector swab 3 inside the mouth. The user then wipes the collector swab 3 across the gums, tongue and the inside of the cheeks to absorb oral fluid. Once the majority of the collector swab 3 is saturated with oral fluid, oral fluid begins to pass to the indicator wick 5 and moves along the wick due to capillary action. As further oral fluid is absorbed by the wick it moves through the band of dye 17, hydrating the dye and carrying it along as it flows. During this process the device 1 is periodically removed from the mouth and checked to establish if the dye can be seen on the visible portion 16 of the wick 5 through the transparent handle 2. Visibility of the dye is used as an indication that an adequate volume of oral fluid has been absorbed.

Figure 7:
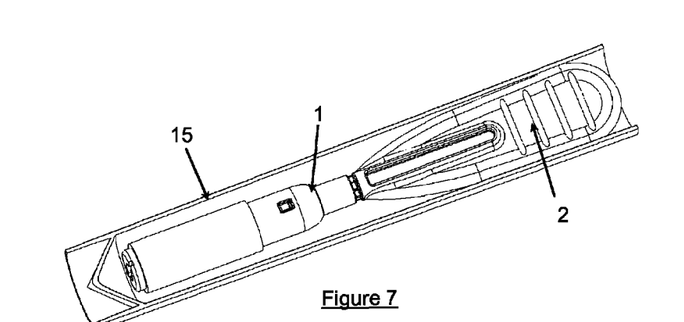
FIG. 7 is a cross-sectional view through an oral fluid collection device inside a container.
Figure 8:
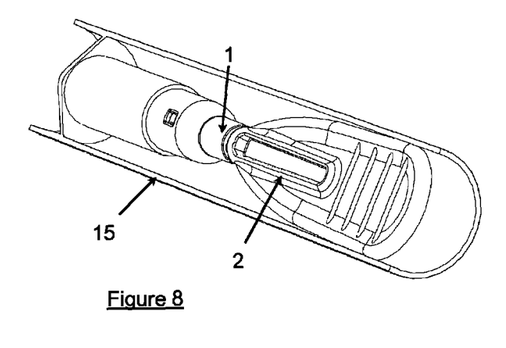
FIG. 8 is a cross-sectional view through an oral fluid collection device inside a container.
Figure 9:
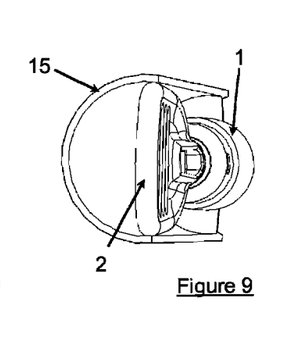
FIG. 9 is a cross-sectional view through an oral fluid collection device inside a container.

Once it has been determined that an adequate volume of oral fluid has been absorbed, the collector swab 3 can be inserted into a container or collection vessel (not shown) containing a suitable buffer solution. If necessary, the user can then separate the handle 2 from the device 1 by snapping the handle 2 at the break-off point 7 such that the collector swab 3 can be sealed inside the collection vessel. Alternatively, if the entire device 1 is to be placed inside the collection vessel, the device 1 can be provided with means for holding it in place inside the collection vessel, such that the vessel can be tilted in order to pour out the oral fluid-buffer mixture without the device 1 falling out. For example, this could be achieved by way of a snap fit or interference fit between the handle of the device and the inside of the vessel. FIGS. 7, 8 and 9 illustrate an example of the device 1 inside a container 15. The handle 2 of the device 1 is of a sufficient size so as to cooperate with an inner surface of the container, forming an interference fit, in order to retain the device 1 within the container 15 even when the container 15 is tilted or tipped to pour out the oral fluid-buffer mixture.

The device described above provides a rigid core to support the collection swab during manufacture, storage and use, and therefore does not rely on the structural integrity of the swab itself. As a result, the device can make use of a collection swab made from a low density material such as a spun polyester material. Previous oral fluid collection devices have relied on the structural integrity of the swab and therefore have not been able to make use of such a low density materials. The use of a low density swab material provides increased speed of collection and improved analyte recovery. Furthermore, a low density spun polyester swab material will accurately and reliably saturate at a predetermined collection volume to allow the collection of a known sample volume.

In addition, the combination of a hollow cylindrical swab attached to a rigid core provides the added flexibility of being able to accurately tune the surface area and thickness of the swab to absorb a desired volume of oral fluid, which can be indicated by the appearance of colour in the visible part of the indicator wick.

The device described above also ensures that the dye of the indicator wick can be located in a position that requires the sample to pass from the swab to the indicator wick before making contact with the dye. This removes any possibility that the sampled oral fluid could 'bypass' the dye and fill the wick without transferring the dye to the visible part of the indicator wick. Furthermore, the indicator wick is partially shrouded by the opaque parts of the device such that only a portion of the indicator wick can be seen through the transparent parts of the device. This minimises any possible ambiguity in reading the indicator as sample adequacy is only signalled when the dye is visible.

A yet further advantage of the device described above is the relative positioning of the swab and sample adequacy indicator components, whereby the sampled oral fluid can only reach the indicator wick when the majority of the swab is already saturated. In addition, the contact between the two components at this point is minimal thereby providing that the indicator will only 'trigger' once the swab is close to saturation.

Furthermore, the device is relatively simple and cheap to manufacture, a particular important feature given that such devices are intended for a single use and are then disposed of.

It will be appreciated by the person of skill in the art that various modifications may be made to the above-described embodiments without departing from the scope of the present invention. For example, a further variant of the device can be achieved using a co-extruded, dual-density swab with a denser inner section to allow robust attachment to the core portion of the device body whilst still providing a lower density outer sheath to minimise collection time and maximise analyte recovery. In addition, whilst it is preferable that the collection swab, the hollow centre of the collection swab and swab holder are all cylindrical, they may be of an alternate shape, for example, they could have a square or triangular cross-section.

The invention claimed is:

1. An oral fluid collection device comprising:
   a handle;
   a swab holder connected to the handle;
   a swab in the form of a hollow tube of absorbent material coaxially located about the swab holder, such that the swab is supported by the swab holder along the entire length of the swab; and
   a wick within the swab holder and being in fluid communication with the swab, the wick containing a soluble dye for the purpose of providing a fluid adequacy indication during use;
   wherein the swab holder has an at least partially hollow core accommodating said wick, wherein the swab holder further comprises a wall parallel to the longitudinal axis of the swab holder and the longitudinal axis of the swab; wherein the swab holder further comprises an opening passing through the wall of the swab holder into the hollow core in a direction perpendicular to the longitudinal axis of the swab holder and the longitudinal axis of the swab, and a projection on an inner surface of the at least partially hollow core opposite the opening and which is configured to press the wick through the opening and into contact with the swab.

2. The device as claimed in claim 1, wherein the projection is a ramp inclined to press the wick through the opening and into contact with the swab.

3. The device as claimed in claim 1, wherein said swab holder and said handle are formed as two separate parts.

4. A device as claimed in claim 1, wherein the handle is transparent at least in the region of an end of the wick and the swab holder is opaque, and the swab holder obscures a portion of the wick coated or impregnated with said soluble dye.

5. A device as claimed in claim 1, wherein the swab holder is provided with one of a plug or a socket and the handle is provided with the other of a plug or a socket, the swab holder and the handle being connected by means of a mechanical fit formed between the plug and the socket.

6. An oral fluid collection device comprising:
   a handle;
   a swab holder connected to the handle;
   a swab in the form of a hollow tube of absorbent material coaxially located about the swab holder, such that the swab is supported by the swab holder along the entire length of the swab; and
   a wick within the swab holder and being in fluid communication with the swab, the wick containing a soluble dye for the purpose of providing a fluid adequacy indication during use; wherein the swab holder further comprises a wall parallel to the longitudinal axis of the swab holder and the longitudinal axis of the swab;
   wherein the swab holder has an at least partially hollow core, and a capillary passing through the wall of the swab holder into the at least partially hollow core which is configured to carry fluid between the swab and the wick.

7. The device as claimed in claim 6, wherein said swab holder and said handle are formed as two separate parts, and configured to be connected together in use.

8. The device as claimed in claim 7, wherein the handle is substantially transparent at least in the region of an end of the wick and swab holder is opaque.

9. The device as claimed in claim 8, wherein the swab holder obscures a portion of the wick coated or impregnated with said soluble dye.

10. A device as claimed in claim 9, wherein the swab holder is provided with one of a plug or socket and the handle is provided with the other of a plug or a socket, the swab holder and the handle being connected by means of a mechanical fit formed between the plug and the socket.

11. A method of manufacturing an oral fluid collection device, the method comprising:

locating a swab in the form of a hollow tube of absorbent material about a swab holder, such that the swab is supported by the swab holder along the entire length of the swab;

either before or after locating the swab, inserting a wick into a passage within the swab holder such that at one end the wick extends out of an open end of said passage and at the other end, a projection on an inner surface of the passage within the swab holder guides the wick through an opening in the swab holder and into contact with said swab, the wick being at least partially coated or impregnated with a dye; and connecting the swab holder to a handle.

12. The method as claimed in claim 11, wherein the swab is attached to the swab holder using one of:
   a mechanical fit; or
   a plastic welding process such as laser or ultrasonic or microwave welding.

13. The method as claimed in claim 11, wherein the swab holder is connected to the handle using one of:
   a mechanical fit; or
   a plastic welding process such as laser or ultrasonic or microwave welding.

14. The method as claimed in claim 13, wherein the swab holder is connected to the handle using a mechanical fit, the mechanical fit being achieved by the insertion of a plug formed with one of the swab holder or the handle being inserted into a socket formed with the other of the swab holder or the handle.

15. A testing kit comprising:
   an oral fluid collection device comprising a swab, a swab holder, and a handle;
   a container arranged to receive the oral fluid collection device;
   the swab in the form of a hollow tube of absorbent material coaxially located about the swab holder, such that the swab is supported by the swab holder along the entire length of the swab;
   a wick within the swab holder and being in fluid communication with the swab, the wick containing a soluble dye for the purpose of providing a fluid adequacy indication during use,
   wherein the swab holder has an at least partially hollow core accommodating said wick, wherein the swab holder further comprises a wall parallel to the longitudinal axis of the swab holder and the longitudinal axis of the swab; wherein the swab holder further comprises an opening passing through the wall of the swab holder into the at least partially hollow core, and a projection on an inner surface of the at least partially hollow core opposite the opening in a direction perpendicular to the longitudinal axis of the swab holder and the longitudinal axis of the swab, wherein the projection is configured to press the wick through the opening and into contact with the swab; and
   the handle of the oral fluid collection device being arranged to cooperate with an inner surface of the container to retain the oral fluid collection device within the container.

16. The testing kit as claimed in claim 15, the oral fluid collection device being arranged to form a snap fit with the inner surface of the container when the oral fluid collection device is inserted into the container.

17. The testing kit as claimed in claim 15, the oral fluid collection device being arranged to form an interference fit with the inner surface of the container when the oral fluid collection device is inserted into the container.

18. The testing kit of claim 15, wherein the container contains a buffer solution.

* * * * *